United States Patent [19]

Baum et al.

[11] Patent Number: 5,164,411
[45] Date of Patent: Nov. 17, 1992

[54] PYRETHROID COMPOSITIONS

[75] Inventors: Jonathan S. Baum, Pennington, N.J.; Michael S. Glenn, Langhorne, Pa.

[73] Assignee: FMC Corporation, Philadelphia, Pa.

[21] Appl. No.: 784,618

[22] Filed: Oct. 30, 1991

Related U.S. Application Data

[63] Continuation-in-part of Ser. No. 646,534, Jan. 25, 1991, abandoned.

[51] Int. Cl.$^5$ .............. C07C 255/37; A01N 53/00
[52] U.S. Cl. .................. 514/521; 558/407
[58] Field of Search ................ 558/407; 514/521

[56] References Cited

U.S. PATENT DOCUMENTS

| | | | |
|---|---|---|---|
| 4,024,163 | 5/1977 | Elliott et al. | 514/521 X |
| 4,133,826 | 1/1979 | Warnant et al. | 558/407 X |
| 4,136,195 | 1/1979 | Warnant et al. | 558/407 X |
| 4,308,279 | 12/1981 | Smeltz | 558/407 X |
| 4,681,969 | 7/1987 | Williams et al. | 558/407 |
| 4,845,126 | 7/1989 | Hidasi et al. | 514/521 |
| 4,997,970 | 3/1991 | Ager, Jr. | 558/407 X |
| 5,013,754 | 5/1991 | Hidasi et al. | 558/407 X |
| 5,028,731 | 7/1991 | Glenn | 558/407 |
| 5,110,976 | 5/1992 | Hidasi et al. | 558/407 |

*Primary Examiner*—Joseph Paul Brust
*Attorney, Agent, or Firm*—H. Robinson Ertelt; Robert M. Kennedy

[57] ABSTRACT

The four isomer compound derived from racemic cis-/trans-3-(2,2-dichloroethenyl)-2,2-dimethylcyclopropanecarboxylic acid and (S)(cyano)(3-phenoxyphenyl) methanol is twice as effective as cypermethrin against certain insect species, but quite unexpectedly is significantly less toxic to mammals and certain species of fish at rates giving commercial control of target crop insects.

4 Claims, No Drawings

PYRETHROID COMPOSITIONS

This application is a continuation-in-part, of application Ser. No. 646,534, filed Jan. 25, 1991, now abandoned.

This invention relates to pyrethroid insecticides, more particularly to a composition consisting of a novel combination of isomers of (cyano)(3-phenoxyphenyl)methyl 3-(2,2-dichloroethenyl)-2,2-dimethylcyclopropanecarboxylate, commonly known as cypermethrin. Cypermethrin, with three optical centers, is composed of eight isomers.

Following the discovery of photostable pyrethroids by Elliott et al and the high insecticidal activity of the single isomer, (S)(cyano)(3-phenoxyphenyl)methyl (1R,cis)-3-(2,2-dibromoethenyl)-2,2-dimethylcyclopropanecarboxylate (here denominated the 1R-cis-S isomer), reported in Nature (1974) 248, 710 and in U.S. Pat. No. 4,024,163, the scientific and patent literature have been replete with methods for the preparation of single isomers and selected combinations of isomers of cypermethrin, methods of enriching isomer mixtures in the more active isomers, and descriptions of the resulting compositions. U.S. Pat. No. 4,136,195 discloses the 1R-cis-S and 1R-cis-R isomers of cypermethrin. U.S. Pat. No. 4,133,826 discloses a process for the conversion of the 1R-cis-R isomer of cypermethrin to the more active 1R-cis-S isomer. U.S. Pat. No. 4,308,279 discloses a compound comprising substantially equimolar amounts of the 1R-cis-S and 1S-cis-R isomers of cypermethrin and a method of preparing it from the four cis isomers of cypermethrin. U.S. Pat. No. 4,845,126 discloses the corresponding combination of 1R-trans-S and 1S-trans-R isomers of cypermethrin. U.S. Pat. No. 5,028,731 discloses a process for the preparation of certain pyrethroid insecticides, including the compound of the present invention.

Both the single isomer dibromo pyrethroid reported by Elliott et al and cypermethrin, comprising eight isomers, are today large volume articles of commerce, and as noted above, much attention has been given to the preparation of selections of isomers of cypermethrin with greater efficacy than cypermethrin itself. A more active product means a lower rate of application and consequently less pesticide put into the environment. However, enriching a pyrethroid in the more active isomers increases the cost of the product. As a practical matter the producer must be careful not to enrich the product to the point that it would cost the farmer more to treat an acre with the improved product than it would to treat with the unenriched pyrethroid or an alternative product. Nevertheless, incremental improvements can be commercially important, particularly when an improvement in efficacy or reduced impact on the environment can be achieved at no increase in cost to the farmer. The consequence of these considerations is the various attempts to find just the right balance of cypermethrin isomers that would give a significant advantage to the farmer without a disproportionate increase in cost.

Despite the extensive studies of cypermethrin and its isomers and the many publications of single isomers and combinations of isomers of cypermethrin, the novel composition disclosed herein had not been described before the present invention, nor had its advantages been recognized.

In the conventional preparation of cypermethrin the acid portion is prepared as a cis/trans racemic mixture, which is then converted to the acid chloride and reacted with racemic (cyano)(3-phenoxyphenyl)methanol (prepared in situ from 3-phenoxybenzaldehyde and sodium cyanide). It has now been found that the four isomer composition derived from the racemic cis/trans acid chloride and the (S)(cyano)(3-phenoxyphenyl)methanol, which composition is herein denominated sigma-cypermethrin, is twice as effective as cypermethrin against certain insect species, but quite unexpectedly is significantly less toxic to mammals and certain species of fish at rates giving commercial control of target crop insects. Consequently, the use of sigma-cypermethrin in place of cypermethrin (1) reduces by one-half the amount of pesticide applied to the environment, (2) reduces the risk of fish kill resulting from the pesticide entering lakes or streams through runoff, (3) reduces the exposure to pesticides of applicators and those who might enter a treated crop area soon after spraying, (4) reduces the amount of residue that might remain on a harvested crop. Moreover, since sigma-cypermethrin may be prepared as the direct product of the reaction of the racemic cis/trans acid chloride and (S)(cyano)-(3-phenoxyphenyl)methanol, there is no need for the additional step of selective crystallization or epimerization of cypermethrin used in certain prior art preparations of selections of cypermethrin isomers.

In the most commonly used method for the production of 3-(2,2-dichloroethenyl)-2,2-dimethylcyclopropanecarboxylic acid chloride the concentrations of the 1S-cis, 1R-cis, 1S-trans, and 1R-trans isomers are approximately equivalent. For the purposes of this application the cis/trans distribution may be regarded as approximately equivalent if the compound consists of $50\pm5\%$ of each. Unless otherwise specified, the term sigma-cypermethrin means a product having a cis/trans ratio of 45-55/55-45, but will more frequently have a ratio of 48-52/52-48.

When prepared on a large scale, such as in the preparation of what is known in the agricultural chemical industry as "technical product", sigma-cypermethrin, while consisting primarily of the S-isomers of cypermethrin, will contain minor amounts of the R-isomers, owing to the R-content of the (S)(cyano)(3-phenoxyphenyl)methanol as well as unreacted starting material and by-products. For the purposes of this application the S/R isomer ratio in (S)(cyano)(3-phenoxyphenyl)methanol is at least 9/1. For the purposes of this application sigma-cypermethrin means a product consisting essentially of a minimum of 88% total isomers of cypermethrin, and a minimum of 80% S-isomers of cypermethrin, the balance being unreacted starting material, including minor constituents present in the starting materials, and by-products produced in the reaction to form sigma-cypermethrin and containing nothing that will materially affect the utility of the product as a pyrethroid insecticide. A representative sigma-cypermethrin technical product contains 89.1% total cypermethrin isomers and 82.9% S-isomers, and the only other compounds present at 1% or more are 3-phenoxybenzaldehyde, 3.56%, and ($\pm$)(cyano)(3-phenoxyphenyl)methanol, 1.93%.

Methods of preparing esters of (S)(cyano)(3-phenoxyphenyl)methanol are illustrated in the following examples.

3

EXAMPLE 1

Preparation of (S)(cyano)(3-phenoxyphenyl)methyl cis/trans-3-(2,2-dichloroethenyl)-2,2-dimethylcyclopropanecarboxylate

Step A

Preparation of (S)(aminocarbonyl)(3-phenoxyphenyl)methyl cis/trans-3-(2,2-dichloroethenyl)-2,2-dimethylcyclopropanecarboxylate A mixture of 10.7 g (0.044 mole) of (S)-3-phenoxymandelamide (prepared by the method of U.S. Pat. No. 4,146,554) was warmed to 400° C. at which time 8 mL of pyridine was added, causing complete dissolution of the solid that was present in the original mixture. Heating was stopped, and 10.0 g (0.044 mole) of cis/-trans-3-(2,2-dichloroethenyl)-2,2-dimethylcyclopropanecarbonyl chloride in 10 mL of toluene was added dropwise during a 15 minute period. The mixture was stirred at ambient temperature for approximately 17 hours, and then 35 mL of 1N hydrochloric acid was added. After this mixture had stirred for 30 minutes, it was poured into a separatory funnel to which was also added 60 mL of diethyl ether. The organic phase was separated and washed twice with 40 mL of a saturated, aqueous sodium chloride solution. After being dried over anhydrous magnesium sulfate, the solvent was removed under reduced pressure, leaving a golden, viscous residue of (S)-(aminocarbonyl)(3-phenoxyphenyl)methyl cis/trans-3-(2,2-dichloroethenyl)-2,2-dimethylcyclopropanecarboxylate weighing 19.0 g.

Step B

Preparation of (S)(cyano)(3-phenoxyphenyl)methyl cis/trans-3-(2,2-dichloroethenyl)-2,2-dimethylcyclopropane carboxylate To a solution of 19.0 g (0.043 mole) of (S)-(aminocarbonyl)(3-phenoxyphenyl)methyl cis/trans-3-(2,2-dichloroethenyl)-2,2-dimethylcyclopropanecarboxylate in 35 mL of methylene chloride under a nitrogen atmosphere was added 55 mL of pyridine. This mixture was cooled to −5° C., and 12.6 g (0.081 mole) of phosphorus oxychloride in 10 mL of methylene chloride was added dropwise during a 20 minute period. Following completion of this addition, the reaction mixture was stirred at 0° C. for one hour after which it was poured into a mixture of 200 mL of 1N hydrochloric acid and crushed ice. The organic and aqueous phases were separated, and the organic phase was washed in succession with 50 mL of a saturated, aqueous solution of sodium chloride and 1N hydrochloric acid. This solution was dried over anhydrous magnesium sulfate, and the solvent was removed under reduced pressure, yielding a light orange oil weighing 17.7 g as a residue. This oil was passed through a column of Florisil ® adsorbent and eluted with methylene chloride. The fractions containing the desired product were combined, and the solvent was evaporated under reduced pressure, leaving a light yellow oil weighing 12 g as a residue. This residue was determined by HPLC to contain 39.2% of the cis-isomer and 58.0% of the trans-isomer of (S)-(cyano)(3-phenoxyphenyl)methyl 3-(2,2-dichloroethenyl)-2,2-dimethylcyclopropanecarboxylate.

$[\alpha]D^{25} = +15.80°(c=1.06, \text{CHCl}_3);$
$[\alpha]D^{25} = +13.62°(c=1.02, \text{ethanol}):$ Calc'd: C 63.47; H 4.60, N 3.36; Found: C 63.43; H 4.60, N 3.15.

EXAMPLE 2

Preparation of (S)(cyano)(3-phenoxyphenyl)methyl cis/trans-3-(2,2-dichloroethenyl)-2,2-dimethylcyclopropanecarboxylate To a refluxing solution of 136.2 g (66.83% assay, 0.400 mole) of cis/trans-3-(2,2-dichloroethenyl)-2,2-dimethylcyclopropanecarbonyl chloride in 75 mL of heptanes under an argon atmosphere was added 139.7 g (0.406 mole) of a 65.5% solution of (S)(cyano)(3-phenoxyphenyl)methanol (containing 93% S-isomer, 7% R-isomer). The addition required 115 minutes during which the temperature remained in the range of 103°–105° C. An additional 20.8 g (0.060 mole) of the 65.5% solution of (S)(cyano)(3-phenoxyphenyl)methanol was added. Upon completion of addition, the mixture was refluxed for one hour. The mixture was then cooled to 90° C., and 100 mL of a 10% solution of sodium carbonate in water was added. This mixture was stirred for 0.5 hour after which it was maintained at 60° C. for approximately 17 hours to allow complete phase separation to occur. The aqueous phase was separated and discarded. The organic phase was washed once with water, and the solvent was evaporated under reduced pressure, leaving 198.8 g of a liquid residue. Liquid phase chromatographic analysis of this residue determined that it contained 79.6% (S)(cyano)(3-phenoxyphenyl)methyl cis/trans-3-(2,2-dichloroethenyl)-2,2-dimethylcyclopropanecarboxylate. Approximately 175 g of this product was dissolved in 100 mL of toluene. This solution was stirred vigorously for a total of 29.5 hours with a solution 40 g of sodium metabisulfite in 160 mL of water. At the conclusion of this period, the aqueous phase was separated and discarded, and the organic phase was washed with 200 mL of water. The solvent was then evaporated under reduced pressure from the organic phase, leaving a residue weighing 129.8 g. By liquid phase chromatographic analysis this residue was found to contain 92.7% total cypermethrin isomers, 86.2% (S)(cyano)(3-phenoxyphenyl)methyl cis/trans-3-(2,2-dichloroethenyl)-2,2-dimethylcyclopropanecarboxylate and 6.5% R-isomer (isomer content estimated on the basis of the isomer content of the starting alcohol), having a cis/trans ratio of 49/51 (sigma-cypermethrin).

The preparations of sigma-cypermethrin used in the following studies of insecticidal activity, mammalian toxicology, and fish toxicity were prepared by the method exemplified in Example 2, which is the method of U.S. Pat. No. 5,028,731. In each case the S- and R-isomer ratio was estimated based on the S/R ratio of the (S)(cyano)(3-phenoxyphenyl)methanol starting material and the total isomer assay. Subsequent analytical studies have shown these estimates to be reliable and accurate.

Insecticidal Activity

The insecticidal activity of sigma-cypermethrin, was evaluated as follows:

Foliar Evaluation

Cypermethrin and sigma-cypermethrin were tested by foliar application at various concentrations in aqueous solutions containing 9.75% acetone and 0.25% octylphenoxypolyethoxyethanol. Insect species utilized included the cabbage looper (*Trichoplusia ni*), southern armyworm (*Spodoptera eridania*), Mexican bean beetle (*Epilachna varivestis*), tobacco budworm (*Heliothis virescens*), and corn earworm (*Heliothis zea*).

For all insects, pinto beans (*Phaseolus vulgaris*) plants were treated with the test solutions. The test solutions were applied with a sprayer to the upper and lower surfaces of the plant leaves to runoff. The plants were then allowed to dry and were severed at the base of the stem before being placed in cups. Ten second instar individuals of the appropriate insect species, except the tobacco budworm and corn earworm, were placed in each cup and the cup covered. Tests with the tobacco budworm and corn earworm used four replicates with each replicate containing five second instar insects. In all tests, mortality was read 48 hours later. The sigma-cypermethrin used in the foliar evaluations was the product of Example 2.

The $LC_{50}$'s and relative potencies calculated from these results are shown below:

| Test Species | $LC_{50}$'s (ppm) Cypermethrin | $LC_{50}$'s (ppm) Σ-Cypermethrin | Relative Potency |
|---|---|---|---|
| CL | 2.3 | 1.4 | 1.6 |
| MBB | 1.2 | 0.3 | 4.0 |
| SAW | 4.2 | 1.8 | 2.3 |
| TBW | 7.3 | 4.4 | 1.7 |
| TBW-R | 92 | 43 | 2.1 |
| CEW | 7.3 | 3.9 | 1.9 |

CL = cabbage looper (*Trichoplusia ni*)
MBB = southern armyworm (*Spodoptera eridania*)
SAW = Mexican bean beetle (*Epilachna varivestis*)
TBW = tobacco budworm (*Heliothis virescens*)
TBW-R = tobacco budworm strain resistant to pyrethroids
CEW = corn earworm (*Heliothis zea*)

The laboratory test results given above show that sigma-cypermethrin is significantly more effective against a variety of insects than cypermethrin, averaging almost twice (1.9 times) as effective against Lepidoptera and four times as effective against the only Coleoptera tested. As a practical matter this means that sigma-cypermethrin would be expected to be effective in the field at about one half the rate required for cypermethrin itself, and this proves to be the case.

Field Trials

Field trials conducted on cotton in Louisiana, Mississippi, Alabama, and Arizona consisted of a randomized complete block design of four replications per treatment. Plots were a minimum of 0.2 acres, and all applications were by commercial ground equipment with a minimum of 10 gallons total spray solution per acre. The cypermethrin isomer content (weight %) of the several sigma-cypermethrin technical products used in the field trials were as follows:

| Year | Total isomers | S-isomers | cis/trans ratio |
|---|---|---|---|
| 1 | 91.5 | 85 | 54/46 |
| 2 | 88.3 | 82 | 52/48 |
|   | 88.3 | 82 | 51/49 |
| 3 | 89.1 | 82 | 51/49 |

Analysis of the data was based on a seasonal average of multiple evaluations taken over a four to six week period (3–4 applications) in trials for control of *Heliothis* sp. The results are shown below.

COMPARISON OF CYPERMETHRIN AND Σ-CYPERMETHRIN

| Treatment | Rate (lb ai/A) | Year 1* % Hel. Live Larv. | Year 1* % Hel. Sq. Dam. | Year 1* Yield (lb SC/A) | Year 2** % Hel. Live Larv. | Year 2** % Hel. Sq. Dam. | Year 3*** % Hel. Live Larv. | Year 3*** % Hel. Sq. Dam. | Year 3*** Yield (lb SC/A) |
|---|---|---|---|---|---|---|---|---|---|
| Σ-Cypermethrin | 0.013 | — | — | — | — | — | 6 | 3 | 2818 |
|  | 0.022 | 10 | 9 | 2828 | — | — | — | — | — |
|  | 0.026 | — | — | — | 3 | 3 | 5 | 4 | 2778 |
|  | 0.03 | 8 | 9 | 2795 | — | — | — | — | — |
|  | 0.039 | — | — | — | — | — | 5 | 3 | 2692 |
| Cypermethrin | 0.06 | 9 | 9 | 2641 | 2 | 3 | 4 | 3 | 2675 |
| Check | — | 23 | 21 | 2122 | 12 | 15 | 10 | 7 | 2522 |

*Seasonal mean average of 3 trials (MS, LA)
**Seasonal mean average of 4 trials (MS, LA)
***Seasonal mean average of 6-8 trials (MS, LA, AL, GA)
Hel. = *Heliothis virescens* and *Heliothis zea*
Larv = *Larvae*
Hel. Sq. Dam. = squares damaged by *Heliothis*
SC/A = seed cotton per acre Field trials conducted on lettuce in California for evaluation of the control of cabbage looper consisted of a randomized complete block design of four replications per treatment. Applications were made to small plots with $CO_2$ backpack sprayer using a minimum of 10 gallons per acre. Results were converted to percent control based on untreated check plots. The results are shown below.

COMPARISON OF CYPERMETHRIN AND Σ-CYPERMETHRIN

| Treatment | Rate (lb ai/A) | % Cabbage Looper Control Year 1 (DAT)* 3 | Year 1 (DAT)* 7 | Year 2 (DAT)** 3 | Year 2 (DAT)** 7 |
|---|---|---|---|---|---|
| Σ-Cypermethrin | 0.013 | — | — | 98 | 71 |
|  | 0.026 | 83 | 90 | 98 | 91 |
|  | 0.039 | — | — | 100 | 98 |
| Cypermethrin | 0.06 | 61 | 78 | 94 | 81 |

*Average of 2 trials (CA)
**Average of 1 trial (CA)
DAT = days after treatment

Field trials were conducted in Louisiana, North Carolina, Texas, Kentucky, Tennessee, and Illinois to evaluate the control of alfalfa weevil (*Hypera postica*). Small plot trials were used in a randomized block design with four replications per treatment. Applications were made with $CO_2$ backpack sprayers. Results were obtained at 3, 7, and 14 days after treatment (DAT) and were converted to percent control based on the untreated check.

| COMPARISON OF CYPERMETHRIN AND Σ-CYPERMETHRIN | | | | | | | |
|---|---|---|---|---|---|---|---|
| | | % Alfalfa Weevil Control | | | | | |
| | Rate | Year 1 (DAT)* | | | Year 2 (DAT)** | | |
| Treatment | (lb ai/A) | 3 | 7 | 14 | 3 | 7 | 14 |
| Σ-Cypermethrin | 0.01 | — | — | — | 93 | 93 | 85 |
| | 0.015 | — | — | — | 94 | 97 | 94 |
| | 0.022 | 96 | 94 | 96 | 94 | 96 | 94 |
| Cypermethrin | 0.04 | — | — | — | 94 | 96 | 90 |

*Average of 4 trials (LA, NC, TX, KY)
**Average of 6 trials (TN, KY, NC, LA, IL, TX)
DAT = days after treatment In each of the field trials reported above sigma-cypermethrin, at half the rate of cypermethrin, or even lower, generally gave results essentially equivalent to that obtained with cypermethrin applied at the recommended rate, sometimes marginally better, sometimes worse. Even where there might appear to be a marginal advantage for cypermethrin, albeit at twice the rate, sigma-cypermethrin was giving commercially acceptable control.

Toxicology

Sigma-cypermethrin has shown surprising advantages over the parent compound, cypermethrin, in both mammalian toxicology and fish toxicity.

90-Day Feeding Study

In the 90-day feeding study, conducted in compliance with EPA guideline 82-1, the compound under test was administered continuously in the diet to groups of rats for at least ninety days at concentrations of 0, 150, and 1500 ppm to groups of fifteen Sprague-Dawley rats for cypermethrin and 0, 10, 50, 150, 250, 500, and 900 ppm to groups of ten Fisher 344 rats for sigma-cypermethrin. (The rates for sigma-cypermethrin were lower, because it was expected to be more toxic than cypermethrin.) The cypermethrin isomer content (weight %) of the sigma-cypermethrin technical product used in this study was total isomers—88.2%, S-isomers—82%, cis/trans ratio—53/47. Individual body weight and food consumption values were recorded weekly. At termination, hematology and clinical chemistry determinations were conducted and organ weights were obtained for adrenals, brain, heart, kidneys, liver, and ovaries or testes. Histopathological examination of approximately 40 tissues was conducted on all animals in the control group and in the highest dose group in the cypermethrin study and in the highest two groups (500 and 900 ppm) in the sigma-cypermethrin study. In addition, histopathological examination was performed on the lungs, liver, and kidneys of animals in the mid-dose groups of both studies (150 and 500 ppm for cypermethrin and 10, 50, 150, and 250 ppm for sigma-cypermethrin). An ophthalmic examination was conducted on all animals prior to initiation of treatment and prior to final sacrifice.

In this test the "no observable effect level" (NOEL) for cypermethrin was 150 ppm, whereas that for sigma-cypermethrin was 250. If sigma-cypermethrin, approximately twice as toxic to target insects as is cypermethrin, were as toxic to rats as to insects, one would expect the NOEL to be half of the value for cypermethrin, but instead it is more than one and a half times the cypermethrin value. In other words, in this study it took more than three times as much sigma-cypermethrin to show an effect on rats as one would expect from the effect of cypermethrin on insects, if the relative effect of sigma-cypermethrin and cypermethrin on rats were the same as the relative effect on insects.

Multigeneration Study

Multigeneration studies were conducted in compliance with EPA guideline 83-4 and provide information on reproductive parameters as well as neonatal morbidity and mortality for multiple generations. Wistar rats were fed diets, throughout the study, containing 0, 50, 150, and 750 ppm of cypermethrin (the top dose level was 1000 ppm for the first 12 weeks, but was lowered to 750 ppm for the remainder of the study owing to toxicity). Similarly, Sprague-Dawley rats were fed diets containing 0, 7.5, 25, 100, 375, and 750 ppm of sigma-cypermethrin. (Again, the rates are lower for sigma-cypermethrin, because it was expected to be more toxic.) The cypermethrin isomer content (weight %) of the sigma-cypermethrin technical product used in this study was total isomers—89.1%, S-isomers—82%, cis/trans ratio—51/49. Each day the rats were observed for mortality and possible signs of the effects of the test substance. Body weights and food consumption were recorded at regular intervals.

The breeding of parental and subsequent generations in each study was initiated with 30 females. In both studies appropriate dietary concentrations of test material were provided during cohabitation. Exposure of the parental males of each generation continued until a scheduled sacrifice following completion of the cohabitation periods, while exposure of parental females continued through to weaning of pups. Pups were weaned at postnatal day 28 in both studies. Because of excessive mortality that occurred for the 750 ppm $F_1$ generation litters (sigma-cypermethrin) during the 28-day lactation period and the first week postweaning, this group was discontinued at the end of the third week postweaning.

In this study the NOEL for cypermethrin was 50 ppm, that for sigma-cypermethrin—100 ppm. Here, too, rather than showing half the NOEL of cypermethrin, as would be expected from the effect against insects, sigma-cypermethrin has a NOEL twice that of cypermethrin. That is, it took four times as much sigma-cypermethrin to show an effect on rats as one would expect from the effect of cypermethrin on insects, if the relative effect of sigma-cypermethrin and cypermethrin on rats were the same as the relative effect on insects.

Teratology

These tests were conducted in compliance with EPA guideline 83-3 for the purpose of determining the effects of the test materials on pregnancy and in utero development. The test materials were administered via gavage in corn oil once daily to female Sprague-Dawley rats on days 6 through 15 of presumed gestation. There were 25 animals per dose group. Dosages of 0, 17.5, 37.5, and 75 mg/kg for cypermethrin and 0, 5, 12.5, 25, and 35 mg/kg for sigma-cypermethrin were administered. The cypermethrin isomer content (weight %) of the sigma-cypermethrin technical product used in this study was total isomers—89.1%, S-isomers—82%, cis/trans ratio—51/49. The control animals (0 mg/kg) received corn oil during the treatment period. All dosages were adjusted daily on the basis of body weights.

Daily observations of the rats were made during the dosage and postdosage periods. On gestation day 20 to 21 the rats were sacrificed for examination of their uterine contents, including the number of live and dead fetuses and the number of resorptions. Fetuses were subsequently examined for malformations.

In this test the NOEL for cypermethrin was 17.5 mg/kg, that for sigma-cypermethrin—12.5. Thus, in this study the amount of sigma-cypermethrin required to show an effect on rats was only 1.4 times what one would expect from the effect of cypermethrin on insects, if the relative effect of sigma-cypermethrin and cypermethrin on rats were the same as the relative effect on insects. There was no embryotoxic or teratogenic effect at any dose for either compound.

In summary, in these established tests for mammalian toxicology, sigma-cypermethrin showed an unexpected and unobvious advantage over cypermethrin—ranging from 1.4 times to four times the amount of sigma-cypermethrin required to show an effect on rats that one would expect from the effect of cypermethrin on insects, if the relative effect of sigma-cypermethrin and cypermethrin on rats were the same as the relative effect on insects.

Fish Toxicity

Ninety-six-hour flow-through acute toxicity studies of both cypermethrin and sigma-cypermethrin were conducted in the rainbow trout (*Oncorhynchus mykiss*) and in the sheepshead minnow (*Cyprinodon variagatus*) to determine the median-lethal-concentration ($LC_{50}$) resulting from continuous exposure. For the rainbow trout the exposure medium was well water; for the sheepshead minnow, filtered seawater. Each group of 20 fish (10 per replicate aquarium) was exposed either to one of five concentrations of pyrethroid delivered in a diluter system in dimethylformamide (DMF), to 30 $\mu$L/L DMF in the exposure medium (solvent control), or to the exposure medium alone (control). Observations for mortality, morbidity, and other overt signs of toxicity were determined at prescribed intervals. Concentrations of the test materials were measured at the beginning and end of the exposure using a validated HPLC method. The cypermethrin isomer content (weight %) of the sigma-cypermethrin technical product used in this study was total isomers—88.2%, S-isomers—82%, cis/trans ratio—53/47.

The measured concentrations used in the test were:
in sheepshead minnow:
for cypermethrin: 4.61, 2.14, 0,765, 0.601, 0.446 $\mu$g/L
for sigma-cypermethrin: 3.00, 1.79, 0.91, 0.62, 0.28 $\mu$g/L
in rainbow trout:
for cypermethrin: 2.24, 1.35, 0.719, 0.366, 0.219 $\mu$g/L
for sigma-cypermethrin: 5.27, 2.77, 1.65, 0.82, 0.47 $\mu$g/L The "no observable effect concentration" (NOEC) and $LC_{50}$ values found in the tests were:
in sheepshead minnow:
cypermethrin: NOEC—2.14 $\mu$g/L, $LC_{50}$—3.88 $\mu$g/L
sigma-cypermethrin: NOEC—1.79 $\mu$g/L, $LC_{50}$—2.37 $\mu$g/L
in rainbow trout:
cypermethrin: NOEC—0.366 $\mu$g/L, $LC_{50}$—0.897 $\mu$g/L
sigma-cypermethrin: NOEC—0.47 $\mu$g/L, $LC_{50}$—0.69 $\mu$g/L Since sigma-cypermethrin is about twice as toxic to commercially important insects as cypermethrin, if it were also twice as toxic to fish the $LC_{50}$'s for sigma-cypermethrin would be expected to be one-half the value of that for cypermethrin. Stated another way, the ratio of the cypermethrin $LC_{50}$ to the sigma-cypermethrin $LC_{50}$ would be expected to be 2.0. Any lower ratio means that sigma-cypermethrin is less toxic to fish than would be expected from its toxicity to insects. The ratio for rainbow trout is 1.3, that for sheepshead minnow, 1.64. Thus sigma-cypermethrin is less toxic to these two species of fish than would be expected from the relative toxicities of the two products to insects.

In summary, sigma-cypermethrin, is twice as effective as cypermethrin against certain insect species that attack major crops, but is significantly less toxic to mammals and certain species of fish at rates giving commercial control of target crop insects. Consequently, using sigma-cypermethrin in place of cypermethrin reduces by one-half the amount of insecticide applied to the environment, reduces the risk of fish kill resulting from the insecticide entering lakes or streams through runoff, reduces the exposure to the insecticide of applicators and those who might enter a treated crop area soon after spraying, and reduces the amount of residue that might remain on a harvested crop. Moreover, any residue of sigma-cypermethrin that might remain on a harvested crop would be expected to be significantly less toxic then the residue of cypermethrin applied to achieve the same level of protection against crop insects, and cypermethrin itself is of relatively low mammalian toxicity for a crop insecticide.

We claim:

1. A cypermethrin composition consisting of a mixture of the 1S-cis-S, 1R-cis-S, 1S-trans-S, and 1R-trans-S isomers in which the isomers are present in approximately equal concentrations, which contains at least 88% total cypermethrin isomers and at least 80% S-isomers of cypermethrin, and which has a cis/trans ratio in the range of 45/55 to 55/45.

2. The product of the reaction of racemic, cis/trans 3-(2,2-dichloroethenyl)-2,2-dimethylcyclopropanecarboxylic acid chloride with (cyano)(3-phenoxyphenyl)methanol in which the S/R isomer ratio is at least 9/1.

3. A composition comprising a composition of claim 1 in admixture with one or more agriculturally acceptable adjuvants.

4. A method of controlling insects which comprises applying to the insects or to the locus in which insects are expected to be found an insecticidally effective amount of a composition of claim 3.

* * * * *